United States Patent

Lodeng et al.

[11] Patent Number: 5,997,826
[45] Date of Patent: *Dec. 7, 1999

[54] REACTOR FOR CATALYTIC DEHYDROGENATION OF HYDROCARBONS WITH SELECTIVE OXIDATION OF HYDROGEN

[75] Inventors: Rune Lodeng; Pal Soraker, both of Trondheim, Norway

[73] Assignee: Den norske stats oljeselskap a.s., Stavanger, Norway

[*] Notice: This patent issued on a continued prosecution application filed under 37 CFR 1.53(d), and is subject to the twenty year patent term provisions of 35 U.S.C. 154(a)(2).

[21] Appl. No.: 08/860,069
[22] PCT Filed: Dec. 18, 1995
[86] PCT No.: PCT/NO95/00236
  § 371 Date: Aug. 5, 1997
  § 102(e) Date: Aug. 5, 1997
[87] PCT Pub. No.: WO96/19424
  PCT Pub. Date: Jun. 27, 1996

[30] Foreign Application Priority Data

Dec. 22, 1994 [NO] Norway .................................. 944982

[51] Int. Cl.[6] .............................. B01J 08/04; B01J 10/00; B01J 8/02; B01J 35/02
[52] U.S. Cl. ........................... 422/190; 422/191; 422/220
[58] Field of Search ..................................... 422/190, 191, 422/220

[56] References Cited

U.S. PATENT DOCUMENTS 3,502,737  3/1970  Ghublikian .
3,855,330  12/1974  Mendelsohn .
4,778,941  10/1988  Tagamolila .
4,806,624  2/1989  Herber et al. .
4,891,464  1/1990  Staggs .
5,043,500  8/1991  Tagamolila .

FOREIGN PATENT DOCUMENTS 0336622  3/1989  European Pat. Off. .

Primary Examiner—Timothy McMahon
Attorney, Agent, or Firm—Kirkpatrick & Lockhart LLP

[57] ABSTRACT

A reactor for catalytic dehydrogenation of dehydrogenatable hydrocarbons, in particular $C_3$ and/or $C_4$ hydrocarbons, in a hydrocarbon-containing stream, with selective oxidation of hydrogen. The reactor comprises serially connected in the flow direction of the hydrocarbon-containing stream: a first catalyst zone (2), an oxygen admixing zone (3) provided with a means (5) for separate feeding of an oxygen-containing gas into the hydrocarbon-containing stream, and a second catalyst zone (4). The oxygen admixing zone (3) has a cross section area in the flow direction of the hydrocarbon-containing stream which is from 0.5% to 75% of the cross section area of each of the two catalysts zones (2, 4), so as to obtain a higher flow velocity in the oxygen-admixing zone (3) than in the catalyst zones. The means (5) for feeding oxygen-containing gas is designed to feed said gas with a flow velocity which is at least 1 m/s and is up to 200 times higher than the flow velocity of the hydrocarbon-containing stream in the oxygen-admixing zone. The oxygen-admixing zone (3) is free of catalyst at least in the region adjacent to the oxygen feeding means (5).

19 Claims, 5 Drawing Sheets

REACTOR FOR CATALYTIC DEHYDROGENATION OF HYDROCARBONS WITH SELECTIVE OXIDATION OF HYDROGEN

FIELD OF INVENTION

The present invention relates to a reactor for catalytic dehydrogenation of dehydrogenatable hydrocarbons, in particular $C_3$ and/or $C_4$ hydrocarbons, to more unsaturated hydrocarbons, with selective oxidation of hydrogen.

BACKGROUND OF THE INVENTION

Catalytic dehydrogenation of hydrocarbons is a well known and commercially important process. The reaction is strongly endothermic. At adiabatic conditions this will result in a lowering of the temperature in the reaction mixture and a consequent lowering of the reaction velocity. Therefore, existing catalytic dehydrogenation processes are dependent on external heat supply to uphold the reaction temperature. Besides, dehydrogenation reactions are subject to equilibrium limitations at typical process conditions.

The above-mentioned limitations have led to the development of autothermal dehydrogenation processes wherein the dehydrogenation is effected in combination with an oxidation of formed hydrogen to water with an oxygen-containing gas. At typical reaction conditions, the exothermic heat generated by the combustion of about half of the formed hydrogen will compensate for the heat loss resulting from the endothermic dehydrogenation reaction. In addition to achieving a desired heat balance, the consumption of hydrogen in the combustion reaction will shift the equilibrium of the desired dehydrogenation reaction in the direction of a higher conversion to dehydrogenated hydrocarbons.

It is strongly desired in such an autothermal dehydrogenation of hydrocarbons that a selective oxidation of hydrogen takes place without any substantial oxidation of hydrocarbons to carbon oxides, as oxidation of hydrocarbons will reduce the efficiency of the dehydrogenation process, due to a direct loss of product and also due to the formation of carbon monoxide. Carbon monoxide may have a deleterious effect on the performance of the dehydrogenation catalyst and thus indirectly reduce the yield of the desired dehydrogenated hydrocarbon.

U.S. Pat. No. 4,914,249 describes a process for autothermal dehydrogenation of a dehydrogenatable hydrocarbon, comprising two dehydrogenation stages and an intermediate oxidation stage for a selective oxidition of hydrogen to water. In this previously known process, the effluent stream from the first dehydrogenation stage, comprising a mixture of dehydrogenated hydrocarbon, unconverted hydrocarbon, hydrogen and steam, is subjected to a selective oxidation of hydrogen on a separate oxidation catalyst in a separate oxidation zone, to which zone the oxygen-containing gas required for the combustion is fed, preferably at a position adjacent to the bed of oxidation catalyst. The effluent from this separate oxidation zone is then subjected to the next dehydrogenation step. Said patent does not specify the flow conditions at which the oxygen-containing gas is introduced into the oxidation zone and mixed with the effluent stream from the first dehydrogenation stage.

U.S. Pat. No. 4,739,124 discloses another autothermal dehydrogenation process. Here, a hydrocarbon represented by ethane is dehydrogenated catalytically in a reactor comprising at least two separate beds of a dehydrogenation catalyst. A feed stream comprising ethane is passed into the first bed of dehydrogenation catalyst maintained at dehydrogenation conditions comprising temperatures in the range of 538° C. to 750° C. The effluent stream from this bed, comprising ethane, ethylene formed as a product and hydrogen formed as a by-product, is cooled and then mixed with an oxygen-containing gas, whereupon the obtained mixture is fed to a separate bed of a selective hydrogen oxidation catalyst maintained at oxidation promoting conditions. The effluent stream from said oxidation bed, which has been heated as a result of the hydrogen combustion, is passed to a second bed of dehydrogenation catalyst similar to the first bed of dehydrogenation catalyst.

The purpose of cooling the effluent stream from the first bed of dehydrogenation catalyst in the process of U.S. Pat. No. 4,739,124, by direct or indirect heat exchange, is to increase the need for combustion of hydrogen in the bed of hydrogen oxidation catalyst. Because a larger part of the hydrogen in the gas mixture has to now be consumed to reach the desired dehydrogenation temperature, the equilibrium concentration of dehydrogenated hydrocarbon i the gas mixture is increased, and the higher equilibrium concentration becomes a driving force for achieving an increased conversion in the dehydrogenation reaction.

The distribution and admixing of the oxygen-containing gas in the process of U.S. Pat. No. 4,739,124 takes place in a catalyst-free zone between the first bed of dehydrogenation catalyst and the bed of hydrogen oxidation catalyst. The oxygen-containing gas may be introduced co-currently through nozzles (shown in the drawing of the patent) or, as also suggested in the patent, through a complex grid of piping having a circular or branching structure (column 8, lines 54 to 58). It is also mentioned that various elements may be placed in the catalyst-free zone to improve the mixing efficiency, but the utilization of such elements is not recommended as it would tend to increase the reactor costs and may increase the pressure drop through the process. There is no suggestion in the patent that the catalyst-free zone should have a restricted flow cross-section area relatively to that of the two beds of dehydrogenation catalyst, for the purpose of increasing the flow velocity in the catalyst-free oxygen-admixing zone.

SUMMARY OF THE INVENTION

It has now been found that, in an autothermal or approximately autothermal process for the dehydrogenation of hydrocarbons with selective oxidation of hydrogen, a more efficient and selective oxidation of the hydrogen can be achieved when the oxygen-containing gas needed for the oxidation is introduced in the process and mixed with the hydrocarbon-containing main stream at certain specific conditions, especially with respect to the flow velocity of the hydrocarbon-containing main stream.

Thus, the present invention provides a reactor for catalytic dehydrogenation of dehydrogenatable hydrocarbons, in particular $C_3$ and/or $C_4$ hydrocarbons, in a hydrocarbon-containing stream, with selective oxidation of hydrogen, comprising serially connected in the flow direction of the hydrocarbon-containing stream:

a first catalyst zone (2) arranged to accommodate a dehydrogenation catalyst which optionally also functions as a hydrogen oxidation catalyst, or a dehydrogenation catalyst and optionally a hydrogen oxidation catalyst in addition thereto, in which latter case said catalyst zone (2) is arranged to accommodate said hydrogen oxidation catalyst in the inlet part of the zone, an oxygen admixing zone (3) provided with a means (5) for separate feeding of an oxygen-containing gas into the hydrocarbon-containing stream, said oxygen-admixing zone (3) being free of catalyst at least in the region adjacent to the oxygen feeding means (5), and a second catalyst zone (4) arranged to accommodate a dehydrogenation catalyst which optionally also functions as a hydrogen oxidation catalyst, or both a dehydrogenation catalyst and a hydrogen oxidation catalyst, in which latter case said catalyst zone (4) is arranged to accommodate said hydrogen oxidation catalyst in the inlet part of the zone.

The characteristic features of the new reactor consist in that:

the oxygen admixing zone (3) has a cross-section area in the flow direction of the hydrocarbon-containing stream which is from 0.5% to 75% of the cross-section area of each of the two catalysts zones (2, 4), so as to obtain a higher flow velocity in the oxygen-admixing zone (3) than in the catalyst zones, and the means (5) for feeding oxygen-containing gas is designed to feed said gas with a flow velocity which is at least 1 m/s and is up to 200 times higher than the flow velocity of the hydrocarbon-containing stream in the oxygen-admixing zone.

The fast, selective and high level hydrogen conversion achieved in the reactor of the invention contributes in an efficient manner to shift the equilibrium of the dehydrogenation reactions in the direction of an increased conversion to the desired unsaturated hydrocarbons. Thus, by using conventional dehydrogenation temperatures, a higher yield of dehydrogenated product can be obtained. Alternatively, a conventional conversion level can be maintained combined with a substantial lowering of the temperature in the dehydrogenation bed. The lowered temperature will result in a decreased sintering of the dehydrogenation catalyst and a reduced coke deposition thereon and provide a more stable dehydrogenation activity for an extended period of time. The need for regeneration of the catalyst is thereby strongly reduced. Also, the selectivity of the process for the formation of the desired unsaturated hydrocarbons will be substantially higher at said lower temperatures than in similar conventional high temperature processes. A lower process temperature is also desirable with a view to the selection of the construction material for the reactor.

In preferred embodiments of the reactor, the oxygen-admixing zone has a cross-section area in the flow direction of the hydrocarbon-containing stream which is from 3% to 50% of the cross-section area of each of the two catalyst zones. In still more preferred embodiments the oxygen-admixing zone 3 has a cross-section area in the flow direction of the hydrocarbon-containing stream which is from 5% to 25% of the cross-section area of each of the two catalyst zones 2, 4.

BRIEF DESCRIPTION OF THE DRAWINGS

The invention will now be described in more detail with reference to the appended drawings, wherein.

DETAILED DESCRIPTION OF THE INVENTION AND PREFERRED EMBODIMENTS

Figure 1:
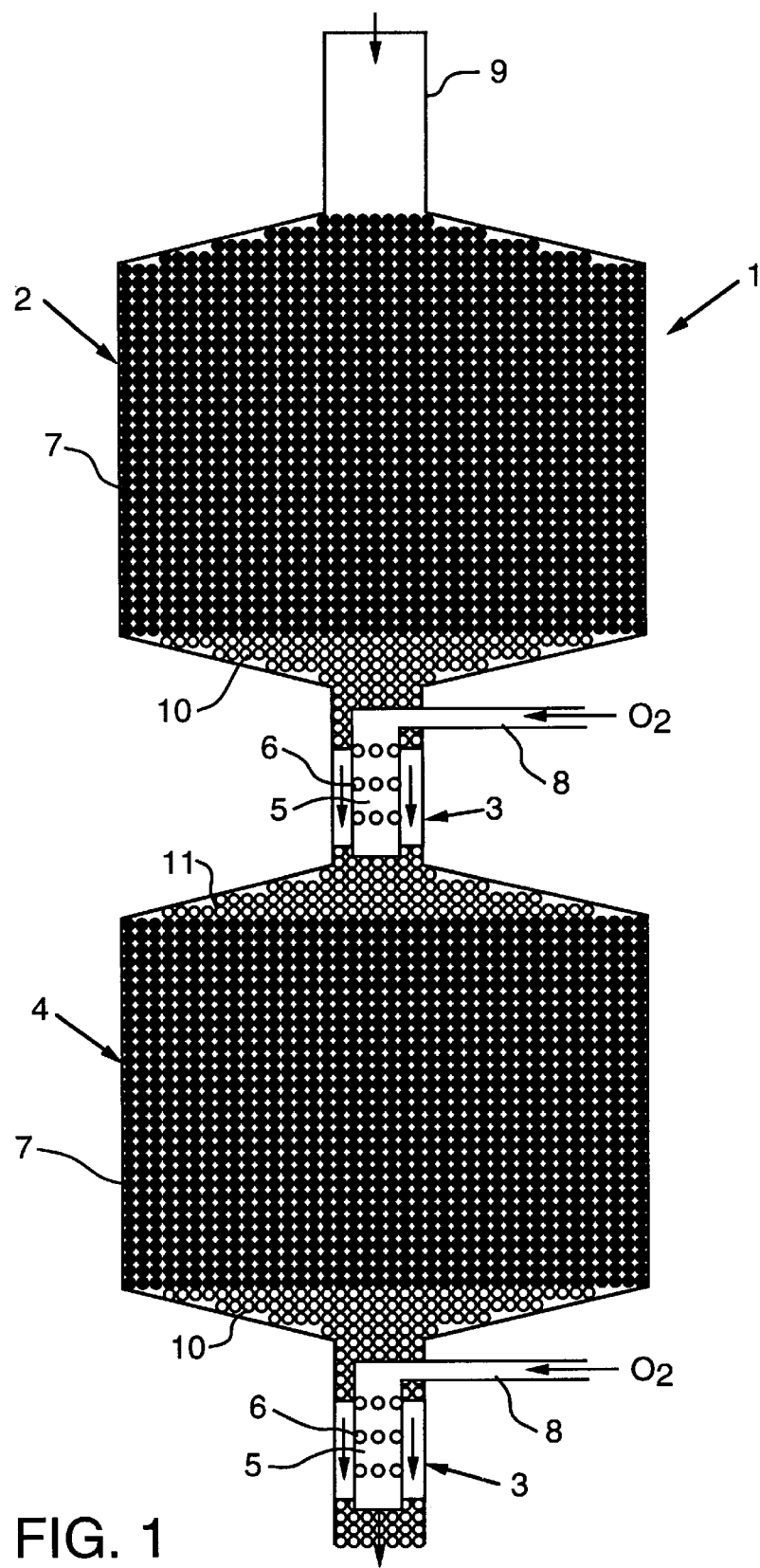
FIG. 1 is a schematic sectional view of an embodiment of the two first catalyst zones and the two first oxygen-admixing zones of a reactor according to the invention having three or more catalyst zones.

FIG. 1 shows a dehydrogenation reactor 1 having an inlet 9 for a feed consisting of a mixture of a dehydrogenatable hydrocarbon, e.g. propane, steam, hydrogen and oxygen, said oxygen being optionally introduced in the form of air or other oxygen-containing gas. The reactor 1 comprises a first catalyst zone 2 and a second catalyst zone 4, both containing a catalyst 7 which serves both as a dehydrogenation catalyst and as a hydrogen oxidation catalyst. An oxygen-admixing zone 3 is arranged between the outlet of the first catalyst zone 2 and the inlet of the second catalyst zone 4, which oxygen-admixing zone is free of catalyst and has a diameter which is substantially smaller than the diameter of the catalyst zones 2 and 4. The oxygen-admixing zone 3 is provided with a means 5 for feeding an oxygen-containing gas, designed as a tube having orifices 6, which orifices may be constituted by nozzles arranged in the walls of the tube. The number of orifices or nozzles may be from one to several thousands, dependent on the importance of an even distribution of the oxygen in the hydrocarbon-containing stream, which latter will also be referred to as the "main stream". The tube 5 or parts thereof may optionally have porous walls. The oxygen-feeding means 5 has an inlet 8 for oxygen-containing gas, which inlet extends laterally through the wall of the oxygen-admixing zone 3. By said feeding means 5 having its inlet for the oxygen-containing gas mounted laterally into the oxygen-admixing zone 3, a good temperature control can be achieved for the admixing of oxygen into the main stream. A similar oxygen-admixing zone 3 is arranged downstream of catalyst zone 4.

Adjacent to the outlet region of each of the two catalyst zones 2 and 4, the shown reactor embodiment has a bed 10 of inert particles, e.g. quartz particles, for the purpose of preventing oxygen which is introduced into the oxygen-admixing zone 3 downstream of the catalyst zone from back-flowing into said catalyst zone against the flow direction of the main stream. A similar bed 11 of inert particles is provided in the inlet region of the second catalyst zone 4 for the purpose of ensuring a good mixing of the propane-containing main stream with the oxygen-containing gas before the mixture reaches the downstream catalyst. Although said layers 10 and 11 of inert particles bring about advantages, they are not strictly required in the reactor. The inlet and outlet regions of the catalyst zones are preferably tapered to ensure favourable flow conditions in the transition regions between reactor sections having different flow cross-section areas.

After having passed through the first catalyst zone 2, the first oxygen-admixing zone 3 and the second catalyst zone 4 the dehydrogenated hydrocarbon-containing product stream would have been removed from the reactor if the reactor had only two catalyst zones. However, instead of an outlet for the dehydrogenated hydrocarbon product downstream of the second catalyst zone, FIG. 1 shows a second oxygen-admixing zone 3, implying that the reactor shown in FIG. 1 includes at least one additional catalyst zone.

In the embodiment shown in FIG. 1, the catalyst zones 2 and 4 contain a catalyst serving both as a dehydrogenation catalyst and a hydrogen oxidation catalyst. As an alternative, however, separate dehydrogenation and hydrogen oxidation catalysts could be used. In such a case, a separate hydrogen oxidation catalyst would be placed in the first catalyst zone 2, in the second catalyst zone 4, and in subsequent catalyst zones, in a relatively narrow bed between the bed of inert particles 11 and the bed of catalyst 7. Catalyst 7 would in this case be a plain dehydrogenation catalyst.

The separate hydrogen oxidation catalyst bed may consist of catalyst particles or an oxidation mesh. The selective combustion of hydrogen to water will take place in this hydrogen oxidation catalyst bed. Particles having a low surface area and large pores are ideal for preventing problems due to restrained pore diffusion, and a resulting prolonged dwelling time in the catalyst bed for parts of the gas mixture, since such particles will favour the more rapid reaction, which is the combustion of hydrogen. Thus, competing slow reactions between oxygen and the hydrocarbons in the main stream are suppressed.

Figure 2:
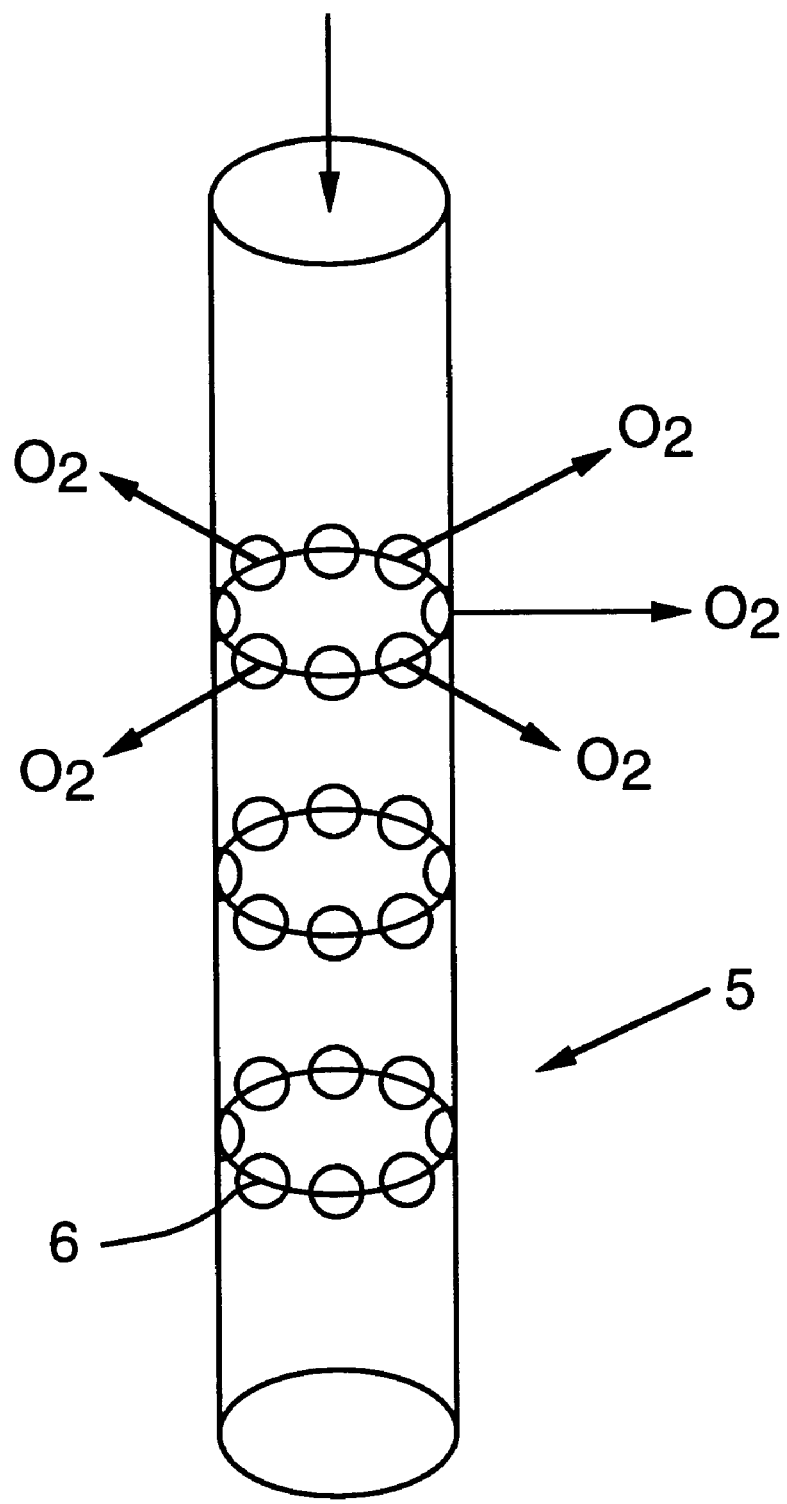
FIG. 2 is a schematic sectional view of a nozzle tube utilized in each of the oxygen-admixing zones of the reactor shown in FIG. 1.

FIG. 2 shows an embodiment of the nozzle tube 5 mounted in the oxygen-admixing zone 3 of the reactor shown in FIG. 1. Orifices 6 are provided in the nozzle tube, which orifices can be shaped as nozzles, e.g. venturi nozzles. Venturi nozzles provide a higher flow velocity of the oxygen-containing gas than simplle orifices in the walls of the nozzletube at equal pressure drop and may therefore be preferable to simple orifices.

Figure 3:
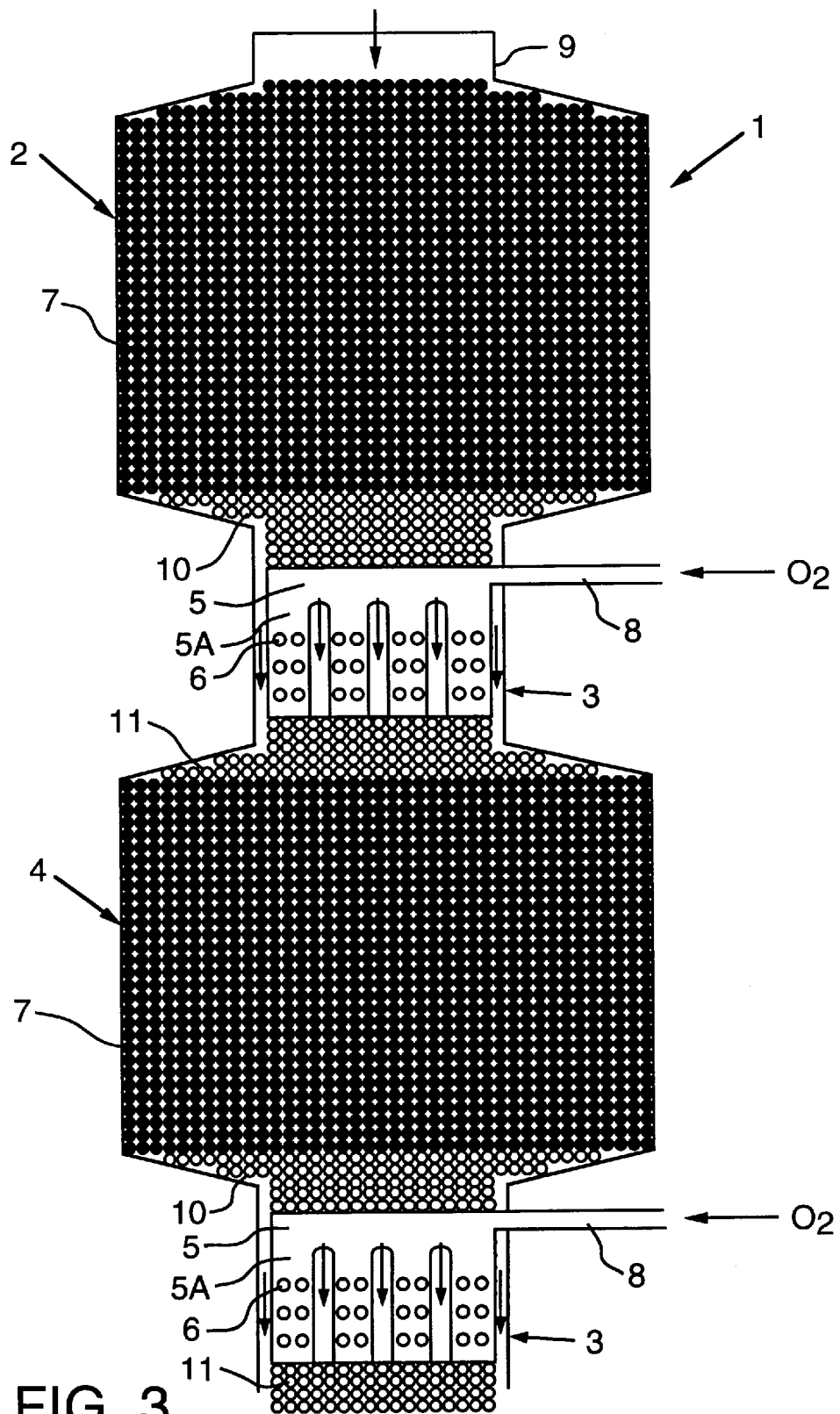
FIGS. 3 to 5 show reactor embodiments similar to the one shown in FIG. 1, with different designs of the oxygen-admixing zones.

FIG. 3 shows a reactor embodiment similar to the one shown in FIG. 1, except that the means 5 for feeding oxygen-containing gas has several nozzle tubes 5A instead of a single tube. Several nozzle tubes in the oxygen-admixing zone will secure a more even distribution of the oxygen in the main stream and thus reduce the risk of high local oxygen concentrations and the consequent risk of explosion. However, by using several nozzle tubes 5A the construction becomes more complex than with a single nozzle tube and maintenance may then be more difficult.

Figure 4:
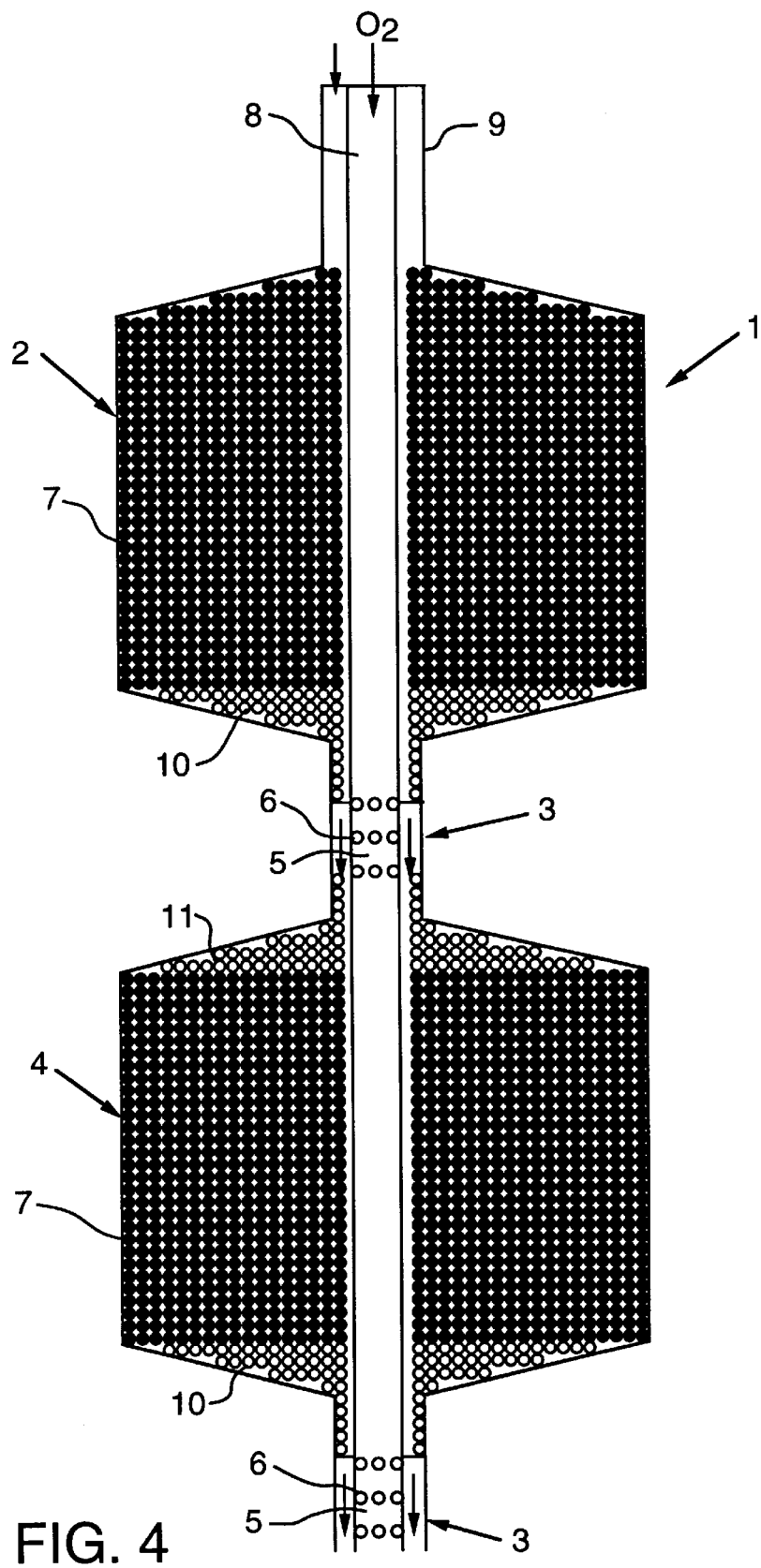

FIG. 4 shows a reactor embodiment similar to the one shown in FIG. 1, except that the means 5 for feeding oxygen-containing gas comprises a nozzle tube extending centrally through the length of the reactor. Said nozzle tube is provided with orifices or nozzles 6 in each of the two oxygen-admixing zones 3. In this embodiment of the reactor, the oxygen-feeding tube 5 may easily be removed from the reactor for maintenance and it has only one inlet for the oxygen-containing gas.

Figure 5:
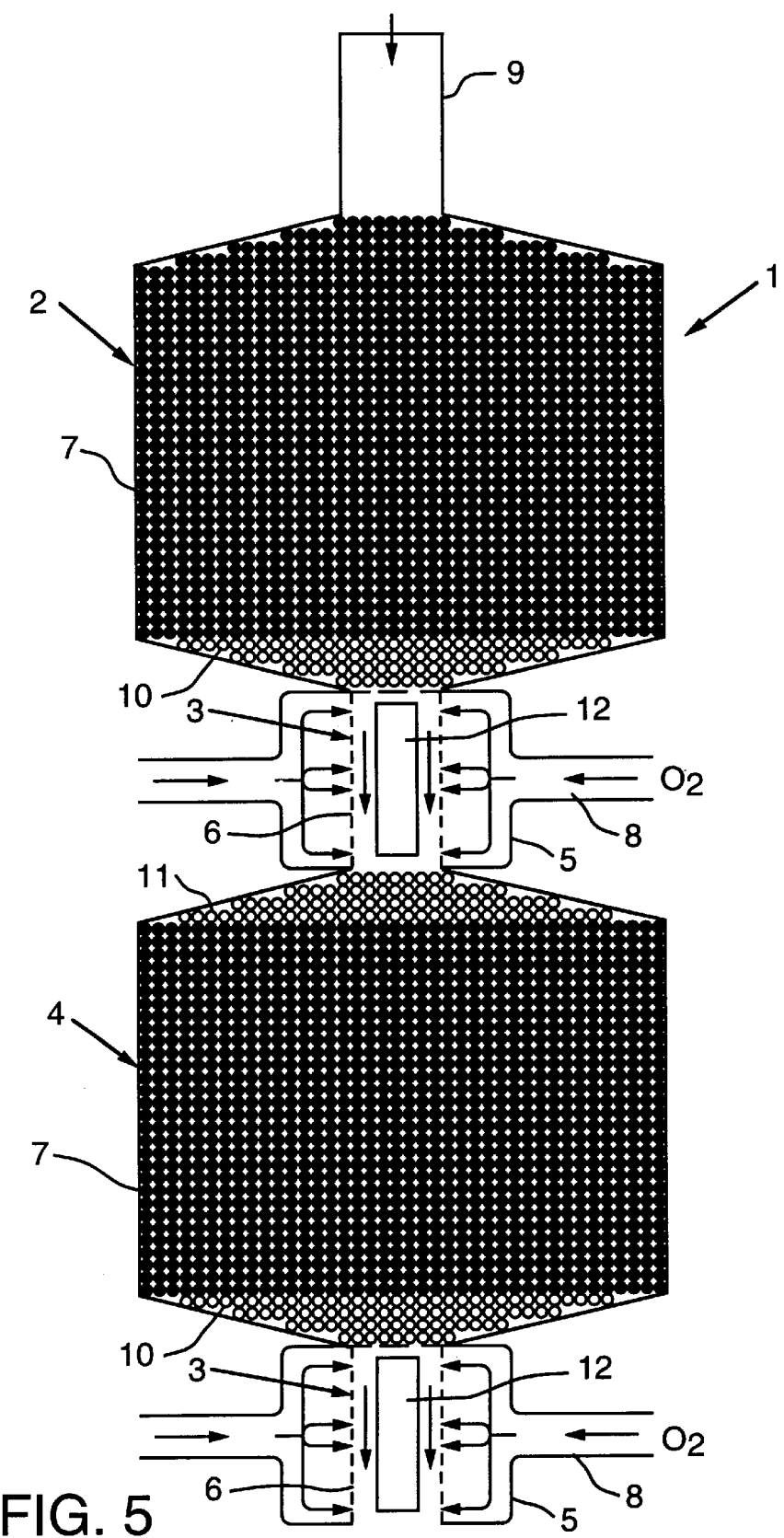

Finally, FIG. 5 shows a reactor embodiment corresponding to the one shown in FIG. 1, except that the means 5 for feeding oxygen-containing gas is arranged outside of the oxygen-admixing zone 3, for feeding the oxygen-containing gas through orifices or nozzles 6 in the outer walls of the oxygen-admixing zone 3. This design of the oxygen-feeding means 5 is simple and allows a good control of the temperature of the introduced oxygen-containing gas all the way to the nozzle inlets.

When the means 5 for feeding oxygen-containing gas is designed as shown in FIG. 5, a massive body 12 may be mounted in a centered position within the oxygen-admixing zone 3 so as to reduce the flow cross-section area of the main stream and thus increase the flow velocity of the main stream.

In a modification of the latter embodiment of the feeding means 5, the massive body 12 may be replaced by e.g. a porous ceramic body coated with a hydrogen oxidation catalyst, so that the combustion of hydrogen will start before the mixture has reached the catalyst zone 4 downstream of the oxygen-admixing zone 3. It is desirable that such combustion takes place on a thin catalyst layer which is not hampered by diffusion restraints, because such thin catalyst layer would strongly promote selective combustion of hydrogen to water. The thin catalyst layer on the ceramic body may consist e.g. of a powder of the catalyst impregnated on the ceramic body.

The reactor of the invention may suitable have 2 to 10 stages, corresponding to the same number of catalyst zones, in a series of alternating catalyst zones and oxygen-admixing zones, wherein the first zone of the reactor is constituted by a catalyst zone 2 and the last zone thereof is constituted by a catalyst zone 4. The number of stages or catalyst zones will be determined by the desired conversion of the hydrocarbon to be dehydrogenated.

The hydrocarbon feed charged to the reactor of the invention at 9, in addition to one or more hydrocarbons, will comprise steam, hydrogen and oxygen, as is usual in essentially auto-thermal processes for the dehydrogenation of hydrocarbons. The oxygen-containing gas introduced in the oxygen-admixing zone 3 of the reactor may suitably have an oxygen concentration of 20% to 100%. The remaining part of the gas may comprise e.g. nitrogen and/or steam. Thus, air may be used as the oxygen-containing gas. The oxygen content of the gas may be as high as 100% without the selectivity for oxidation of hydrogen to water being substantially reduced as compared to oxygen concentrations in the oxygen feed down towards 20%.

As mentioned in the introductory part of the specification, it is strongly desired in autothermal dehydrogenation of hydrocarbons that a selective oxidation of hydrogen takes place, i.e. an oxidation of hydrogen without any substantial concurrent oxidation of hydrocarbons, as oxidation of hydrocarbons will reduce the efficiency of the dehydrogenation process.

The added oxygen needs a certain time to be sufficiently admixed with the main stream, before the mixture is contacted with the catalyst which catalyzes the combustion of hydrogen. The mixing time is defined as the time it takes for the main stream to pass from the nozzle outlet to the catalyst. It is determined by the distance from the nozzle to the catalyst and by the flow velocity of the main stream.

For the oxidation of hydrogen to take place with a high selectivity, it has been found that the mixing time must be sufficiently short that no substantial conversion of the oxygen in gaseous phase occurs before the mixture is contacted with the catalyst. Oxygen conversion occurring in gaseous phase, before the mixture is contacted with the catalyst, has an undesirably low $O_2$ selectivity for $H_2O$ and will result in an undesirably high degree of oxidation of hydrocarbons. However, as soon as the mixture is contacted with the catalyst, oxidation of hydrogen to water takes place almost spontaneously and with a high selectivity, provided that the oxygen is well admixed with the main stream.

Tests carried out by the inventors have shown that the best results are achieved when the mixing time is less than 15 milliseconds (ms).

The inventors have also found that a high flow velocity of the main stream in the oxygen-admixing zone 3 is essential to achieve a complete admixing of the added oxygen with the main stream. Thus, simulated dehydrogenations of propane carried out by the inventors have shown that an increase of the flow velocity of the main stream within actual flow velocity ranges results in a substantial increase of the $O_2$ selectivity for $H_2O$. By way of example, an increase of the flow velocity of the main stream from 0.9 m/s to 4.5 m/s resulted in an increase of the $O_2$ selectivity for $H_2O$ of from less than 80% to 95.5%, the mixing time being approximately constant. Such high $O_2$ selectivity for $H_2O$ is assumed to be due to the higher flow velocity of the main stream, resulting in a more complete admixing of the oxygen with the main stream.

It is true that the $O_2$ selectivity for $H_2O$ could be increased somewhat by increasing the mixing time from 11 to 24 ms, viz. from 69% to 87%, but a further increase of the mixing time to 46 ms, with the flow velocity of the main stream being the same, resulted in a reduction of the $O_2$ selectivity for $H_2$ to 80%. Thus, the right solution was not to increase the mixing time but to increase the flow velocity of the main stream, maintaining a short mixing time (11 ms). The flow velocity of the $O_2$ mixture through the nozzle was maintained at a constant value (of about 33 m/s) during the above-mentioned experiments, and the mixing time was adjusted by varying the distance between the outlet of the oxygen-feeding nozzle and the catalyst bed.

According to the invention, the desired high flow velocity of the main stream through the oxygen-admixing zone is achieved by narrowing the flow cross-section area of the oxygen-admixing zone essentially relatively to the flow cross-section area of the catalyst zones. Suitable main stream flow velocities in the oxygen-admixing zone of the reactor of the invention may be in the range of 1 to 50 m/s. The flow velocity of the main stream through the dehydrogenation catalyst beds will be substantially lower, however, than the flow velocity in the oxygen-admixing zone, in order to achieve a high conversion in dehydrogenation of the hydrocarbon.

The velocity at which the oxygen-containing gas is introduced into the oxygen-admixing zone 3 through the orifices or nozzles 6 appears to be less critical to the achievement of a complete admixing of the oxygen than the flow velocity of the main stream in the oxygen-admixing zone, provided that the oxygen-containing gas is fed at a flow velocity at a certain level, e.g. of the order of magnitude of 35 m/s or higher, e.g. up to 200 m/s. Any further increase of the flow velocity of the oxygen-containing gas does not appear to result in any substantially improved selectivity for the oxidation of hydrogen to water.

Experiments have shown that a co-current, axial introduction of the oxygen into the main stream does not result in any substantially poorer mixing or reduced selectivity of the oxidation of hydrogen to water than an introduction of the oxygen-containing gas through radial nozzles in a direction transversal to the flow direction of the main stream, provided the flow velocity of the oxygen-containing gas is of the above-mentioned order of magnitude. It has been established, however, that the oxygen-containing gas is distributed somewhat better by using radial nozzles and such introduction of the oxygen is therefore preferred, not the least because it reduces the risk of high local oxygen concentrations.

Operation conditions at which the reactor of the invention may be operated in a process for the dehydrogenation of propane to propene are given below. It is to be noted, however, that the reactor of the invention is not limited to being useful for the dehydrogenation of propane but is also useful for the dehydrogenation of other dehydrogenatable hydrocarbons.

Reactor pressure: 0,5–3 bars

Dehydrogenation temperature: 400–700° C.

Oxidation temperature: 25–700° C.

Hydrogen conversion: 10–100%

Main stream velocity: 0,1–10 m/s

Velocity of oxygen-containing gas at nozzle outlet: 1 m/s - crit. velocity

Mixing time: <15 ms

As dehydrogenation catalyst and as hydrogen oxidation catalyst, any such previously known catalysts may be used. In the experiments carried out for assessing the present invention, catalysts were used which contained Pt (0.7–1.02% by weight), Sn (0.5–1.15% by weight) and Cs (1.72–3.86% by weight) on $\theta$-$Al_2O_3$, as well as a catalyst containing 0.3% by weight of Pt and 1.2% by weight of tin on a mixed oxide Mg(Al)O. Said catalysts act both as a dehydrogenation catalyst and as a hydrogen oxidation catalyst.

Experiments have shown that oxygen can be effectively admixed with the main stream at temperatures up to the range of 550 to 600° C. without the selectivity for water being reduced.

The overall reaction in the dehydrogenation of the dehydrogenatable hydrocarbons may be autothermal, exothermic or endothermic.

In a process for the dehydrogenation of propane to propene, the overall reaction is autothermal when the oxygen oxidizes about half of the hydrogen formed in the dehydrogenation reaction. The dehydrogenation is then typically carried out at 580–650° C.

In a process for the dehydrogenation of propane, the overall reaction is exothermic when the oxygen oxidizes more than half of the hydrogen formed in the dehydrogenation reaction. In such case, the dehydrogenation is carried out at low temperature (400–580° C.), and the driving force for achieving a high conversion of the propane is generated by combustion of hydrogen. A low hydrogen concentration shifts the reaction equilibrium in the direction of a higher conversion of the propane to propene.

In a process for the dehydrogenation of propane, the overall reaction is endothermic when the oxygen oxidizes less than half of the hydrogen formed in the dehydrogenation reaction. At high concentrations of the propene product, e.g. in the last stages of a multistage reactor, there will be a higher risk of undesired gaseous phase reactions between oxygen and propene than in the preceding stages. It may therefore be advisable to limit the amount of added oxygen in said last stages so as to achieve an endothermic overall reaction.

EXAMPLE

A dehydrogenation of propane to propene at a pressure of 1 bar and a temperature of about 600° C., combined with combustion of hydrogen with an oxygen-containing gas, was carried out at a laboratory scale. The test was carried out in a reactor of the design shown schematically in FIG. 4, comprising a first catalyst zone 2, a second catalyst zone 4 and an intermediate oxygen-admixing zone 3. Both catalyst zones contained a catalyst consisting of 0.3% by weight of Pt and 1.2% by weight of Sn on a carrier consisting of Mg(Al)O, prepared as disclosed in international patent application No. PCT/NO94/00102. The flow cross-section area of the oxygen-admixing zone was about 5% of the flow cross-section area of each of the two catalyst zones. The amounts of catalyst in the catalyst zones, the composition of the propane-containing feed stream (the main stream) and the composition of the oxygen-containing stream were as follows:

| Amount of catalyst: | |
| --- | --- |
| Catalyst zone 2 (g) | 19.1 |
| Catalyst zone 4 (g) | 58.5 |

-continued

| Main stream: | |
|---|---|
| $C_3H_8$ (N ml/min) | 1000 |
| $H_2$ (N ml/min) | 400 |
| $N_2$ (N ml/min) | 45 |
| $O_2$ (N ml/min) | 130 |
| $H_2O$ (N ml/min) | 1040 |
| $O_2$-containing stream: | |
| $O_2$ (N ml/min) | 130 |
| $N_2$ (N ml/min) | 45 |

The propane-containing feed stream (the main stream) was introduced with a gas space velocity per hour GHSV of 2100 N ml $g^{-1}$ $h^{-1}$. The flow velocities in the reactor were:

Catalyst zone 2: 0.51 m/s

Oxygen-admixing zone 3: 8.4 m/s

Catalyst zone 4: 0.51 m/s

Oxygen-containing gas through the nozzles: 47 m/s

The above test conditions resulted in a mixing time in the oxygen-admixing zone of 6 milliseconds (ms). The oxidation temperature in the inlet region of the catalyst zone 4 was about 400° C.

The hydrogen conversion in catalyst zone 2 was 65%, whereas the hydrogen conversion in catalyst zone 4 was 50%. After 20 hours of operation the results were:

Conversion of propane: 55%

C-selectivity for propene: 94 mol %

Yield of propene: 51.7 mol %

Conversion of oxygen: 100%

$O_2$-selectivity for water: 87%

The results achieved with the reactor design employed in this example are markedly improved relatively to results achieved with previously known reactor designs which do not provide any substantial difference between the flow velocity of the main stream in the catalyst zones and its flow velocity in the oxygen-admixing zone(s). When the flow velocity of the main stream is substantially higher in the oxygen-admixing zone than in the catalyst zones, as in this example, the hydrogen is oxidized more selectively to water, and the dehydrogenation reaction is maintained at a high conversion level with a good selectivity for propene.

We claim:

1. A reactor for catalytic dehydrogenation of dehydrogenatable hydrocarbons, in particular $C_3$ and or $C_4$ hydrocarbons, in a hydrocarbon-containing stream, with selective oxidation of hydrogen, comprising serially connected in the flow direction of the hydrocarbon-containing stream:

a first catalyst zone arranged to accommodate a dehydrogenation catalyst which optionally also functions as a hydrogen oxidation catalyst, or a dehydrogenation catalyst and optionally a hydrogen oxidation catalyst in addition thereto, in which latter case said catalyst zone is arranged to accommodate said hydrogen oxidation catalyst in the inlet part of the zone, an oxygen admixing zone provided with a means for separate feeding of an oxygen-containing gas into the hydrocarbon-containing stream, said oxygen-admixing zone being free of catalyst at least in the region adjacent to the oxygen feeding means, and a second catalyst zone arranged to accommodate a dehydrogenation catalyst which also functions as a hydrogen oxidation catalyst, or both a dehydrogenation catalyst and a hydrogen oxidation catalyst, in which latter case said catalyst zone is arranged to accommodate said hydrogen oxidation catalyst in the inlet part of the zone, characterized in that:

the oxygen admixing zone has a cross-section area in the flow direction of the hydrocarbon-containing stream which is from 3% to 50% of the cross-section area of either one of the two catalysts zones, so as to obtain a higher flow velocity in the oxygen-admixing zone than in the catalyst zones, wherein the flow velocity in the oxygen mixing zone is from 1 m/s to 50 m/s;

the means for separate feeding being a gas supply source having at least one outlet, said source configured such that the flow velocity of the oxygen-containing gas into the hydrocarbon-containing stream in the oxygen-admixing zone is 35 m/s or higher, and the distance from the at least one outlet of the means for separate feeding of an oxygen-containing gas into the hydrocarbon-containing stream in the oxygen-admixing zone to the catalyst in the second catalyst zone is such that it is traversed by the hydrocarbon-containing stream in less than 15 milliseconds (ms).

2. A reactor according to claim 1, characterized in that the oxygen-admixing zone has a cross-section area in the flow direction of the hydrocarbon-containing stream which is from 5% to 25% of the cross-section area of either one of the two catalyst zones.

3. A reactor according to claim 2, characterized in that the means for feeding oxygen-containing gas to the oxygen-admixing zone is designed to feed said gas in a direction which is transverse to the flow direction of the hydrocarbon-containing stream.

4. A reactor according to claim 1, characterized in that the means for feeding oxygen-containing gas to the oxygen-admixing zone is designed to feed said gas in a direction which is transverse to the flow direction of the hydrocarbon-containing stream.

5. A reactor according to claim 4, characterized in that the means for feeding oxygen-containing gas is centered in a cross-section of the oxygen-admixing zone and comprises at least one tube provided with at least one of orifices or radially extending nozzles.

6. A reactor according to claim 5, characterized in that the means for feeding oxygen-containing gas to the oxygen-admixing zone comprises a tube, which tube extends throughout the reactor, and is provided with at least one of orifices or nozzles in the oxygen-admixing zone.

7. A reactor according to claim 4, characterized in that the means for feeding oxygen-containing gas is arranged outside the oxygen-admixing zone for feeding the oxygen-containing gas through at least one of orifices or nozzles in the outer wall of said zone.

8. A reactor according to claim 1, characterized by there being arranged, adjacent to at least one of the outlet of the first catalyst zone or to the inlet of the oxygen-admixing zone, a layer of solid particles for the purpose of preventing back-flow of oxygen from the oxygen-admixing zone into the first catalyst zone.

9. A reactor according to claim 3, characterized in that the means for feeding oxygen-containing gas is centered in a cross-section of the oxygen-admixing zone and comprises at least one tube provided with at least one of orifices or radially extending nozzles.

10. A reactor according to claim 4, characterized in that the means for feeding oxygen-containing gas to the oxygen-admixing zone comprises a tube, which tube extends throughout the reactor, and is provided with at least one of orifices or nozzles in the oxygen-admixing zone.

11. A reactor according to claim 3, characterized in that the means for feeding oxygen-containing gas is arranged outside the oxygen-admixing zone for feeding the oxygen-containing gas through at least one of orifices or nozzles in the outer wall of said zone.

12. A reactor according to claim 6, characterized by there being arranged, adjacent to at least one of the outlet of the first catalyst zone or to the inlet of the oxygen-admixing zone, a layer of solid particles for the purpose of preventing back-flow of oxygen from the oxygen-admixing zone into the first catalyst zone.

13. A reactor according to claim 7, characterized by there being arranged, adjacent to at least one of the outlet of the first catalyst zone or to the inlet of the oxygen-admixing zone, a layer of solid particles for the purpose of preventing back-flow of oxygen from the oxygen-admixing zone into the first catalyst zone.

14. A reactor according to claim 9, characterized by there being arranged, adjacent to at least one of the outlet of the first catalyst zone or to the inlet of the oxygen-admixing zone, a layer of solid particles for the purpose of preventing back-flow of oxygen from the oxygen-admixing zone into the first catalyst zone.

15. A reactor according to claim 1 wherein the flow velocity in the means for separate feeding of oxygen-containing gas into the hydrocarbon-containing stream in the oxygen-admixing zone is in the range of 35 m/s to about 200 m/s.

16. A reactor for catalytic dehydrogenation of dehydrogenatable hydrocarbons, in particular $C_3$ and or $C_4$ hydrocarbons, in a hydrocarbon-containing stream, with selective oxidation of hydrogen, comprising serially connected in the flow direction of the hydrocarbon-containing stream:

a first catalyst zone arranged to accommodate a dehydrogenation catalyst which also functions as a hydrogen oxidation catalyst, or a dehydrogenation catalyst and a hydrogen oxidation catalyst in addition thereto, in which latter case said catalyst zone is arranged to accommodate said hydrogen oxidation catalyst in the inlet part of the zone, an oxygen admixing zone provided with a means for separate feeding of an oxygen-containing gas into the hydrocarbon-containing stream, said oxygen-admixing zone being free of catalyst at least in the region adjacent to the oxygen feeding means, and a second catalyst zone arranged to accommodate a dehydrogenation catalyst which also functions as a hydrogen oxidation catalyst, or both a dehydrogenation catalyst and a hydrogen oxidation catalyst, in which latter case said catalyst zone is arranged to accommodate said hydrogen oxidation catalyst in the inlet part of the zone, characterized in that:

the oxygen admixing zone has a cross-sectional area in the flow direction of the hydrocarbon-containing stream which is from 3% to 50% of the cross-sectional area of either one of the two catalysts zones, so as to obtain a higher flow velocity in the oxygen-admixing zone than in the catalyst zones, wherein the flow velocity in the oxygen mixing zone is from 1 m/s to 50 m/s;

the means for separate feeding of oxygen-containing gas into the hydrocarbon-containing stream in the oxygen-admixing zone being a gas supply source having at least one outlet, said source configured such that the flow velocity of said gas is 35 m/s or higher, and the distance from the at least one outlet of the means for separate feeding of an oxygen-containing gas into the hydrocarbon-containing stream in the oxygen-admixing zone to the catalyst in the second catalyst zone is such that it is traversed by the hydrocarbon-containing stream in less than 15 milliseconds (ms).

17. A reactor for dehydrogenation of a hydrocarbon-containing stream, comprising, in series:

a first catalyst zone containing a first dehydrogenation catalyst, and configured such that, in use, the hydrocarbon-containing stream passes through said first catalyst zone at a first velocity;

an oxygen-admixing zone having a cross-sectional area in the flow direction of the hydrocarbon-containing stream that is from 3% to 50% of the cross-sectional area of the first catalyst zone, and configured such that said admixing zone has a second velocity that is greater than said first velocity and ranges from 1 m/s to 50 m/s, said oxygen-admixing zone provided with a separate oxygen-containing gas supply source having at least one outlet in fluid communication with the hydrocarbon-containing stream, said source configured such that the flow velocity of oxygen-containing gas into said admixing zone is 35 m/s or higher; and a second catalyst zone containing a second dehydrogenation catalyst, the distance from said at least one outlet of said source to said second catalyst is such that the distance is traversed by the hydrocarbon-containing stream in less than 15 milliseconds.

18. The reactor of claim 17 wherein said oxygen-admixing zone has a cross-sectional area in the flow direction of the stream which is from 3% to 50% of the cross-sectional area of the second catalyst zone.

19. A method of producing hydrocarbons by passing a hydrocarbon-containing stream through a catalytic dehydrogenation reactor, comprising:

passing a hydrocarbon-containing stream passing through a first catalyst zone at a first velocity;

dehydrogenating the stream in the first catalyst zone by exposing the stream to a first dehydrogenation catalyst contained in the first catalyst zone;

admixing oxygen-containing gas into the stream via an oxygen-containing gas supply outlet in an admixing zone, the flow velocity of oxygen-containing gas being 35 m/s or higher, the stream flowing through the admixing zone at a second velocity that is greater than the first velocity and ranging from 1 m/s to 50 m/s; and dehydrogenating the stream in a second catalyst zone containing a second dehydrogenation catalyst, the stream flowing from the supply outlet to the second catalyst in less than 15 milliseconds.

\* \* \* \* \*